US008865663B2

(12) United States Patent
Toi et al.

(10) Patent No.: US 8,865,663 B2
(45) Date of Patent: Oct. 21, 2014

(54) METHOD FOR THE ADMINISTRATION OF ANTI-CANCER DRUGS

(75) Inventors: Masakazu Toi, Kyoto (JP); Hiroji Iwata, Aichi (JP); Katsumasa Kuroi, Tokyo (JP); Seigo Nakamura, Tokyo (JP); Shinji Ohno, Fukuoka (JP); Norikazu Masuda, Osaka (JP); Kenjiro Aogi, Ehime (JP); Nobuaki Sato, Niigata (JP); Futoshi Akiyama, Tokyo (JP); Masafumi Kurosumi, Saitama (JP); Hitoshi Tsuda, Tokyo (JP)

(73) Assignee: Japan Breast Cancer Research Group, Tokyo (JP)

( * ) Notice: Subject to any disclaimer, the term of this patent is extended or adjusted under 35 U.S.C. 154(b) by 679 days.

(21) Appl. No.: 12/934,146

(22) PCT Filed: Jan. 26, 2009

(86) PCT No.: PCT/JP2009/000277
§ 371 (c)(1),
(2), (4) Date: Sep. 23, 2010

(87) PCT Pub. No.: WO2009/118974
PCT Pub. Date: Oct. 1, 2009

(65) Prior Publication Data
US 2011/0015144 A1    Jan. 20, 2011

(30) Foreign Application Priority Data
Mar. 26, 2008    (JP) .................................. 2008-081723

(51) Int. Cl.
| | |
|---|---|
| A61K 31/704 | (2006.01) |
| G06Q 50/00 | (2012.01) |
| A61P 35/00 | (2006.01) |
| A61K 31/337 | (2006.01) |
| C07K 14/71 | (2006.01) |
| C07K 14/72 | (2006.01) |
| A61K 31/513 | (2006.01) |
| A61K 31/675 | (2006.01) |
| G06F 19/00 | (2011.01) |
| G06Q 50/22 | (2012.01) |

(52) U.S. Cl.
CPC .............. *A61K 31/337* (2013.01); *C07K 14/71* (2013.01); *C07K 14/721* (2013.01); *G01N 2333/723* (2013.01); *G01N 2333/71* (2013.01); *A61K 31/513* (2013.01); *A61K 31/675* (2013.01); *A61K 31/704* (2013.01); *G06F 19/3456* (2013.01); *G06F 19/363* (2013.01); *G06Q 50/22* (2013.01)
USPC ................................................ 514/34; 705/2

(58) Field of Classification Search
None
See application file for complete search history.

(56) References Cited

U.S. PATENT DOCUMENTS
2006/0018910 A1    1/2006 Gualberto et al.

FOREIGN PATENT DOCUMENTS
| JP | 2004-287946 | 10/2004 |
| JP | 2008-506681 | 3/2008 |

OTHER PUBLICATIONS

Toi, et al., Breast Cancer Res Treat., 2008, 110, 531-539.*
Wardley, "Capecitabine: Expanding Options for the Treatment of Patients with Early or Locally Advanced Breast Cancer" The Oncologist (2006) vol. 11 pp. 20-26.*
International Search Report issued Mar. 10, 2009 in International (PCT) Application No. PCT/JP2009/000277.
Adjuvant! Online; Decision making tools for health care professionals (http://www.adjuvantonline.com/index.jsp), © 2008.

* cited by examiner

*Primary Examiner* — Eric Olson
(74) *Attorney, Agent, or Firm* — Wenderoth, Lind & Ponack, L.L.P

(57) ABSTRACT

An administration method comprising: determining a cancer type through (i) first data indicating that an Estrogen Receptor (ER) is negative and a Human Epidermal growth factor Receptor-2 (Her2) is negative, or (ii) second data indicating that at least one of the ER and the Her2 is positive; and when the cancer type is determined through (i) the first data indicating that the ER is negative and the Her2 is negative: first performing a docetaxel administration cycle comprising administrating docetaxel to a patient multiple times at certain intervals; and then performing a 5-fluorouracil, epirubicin, and cyclophosphamide (FEC) administration cycle comprising administrating 5-fluorouracil, epirubicin, and cyclophosphamide to the patient multiple times at certain intervals, and when the cancer type is determined through (ii) the second data indicating that at least one of the ER and Her2 is positive: first performing the FEC administration cycle; and then performing the docetaxel administration cycle.

1 Claim, 5 Drawing Sheets

FIG. 3

| ER/Her2 | +/+ | +/− | −/+ | −/− |
|---|---|---|---|---|
| A → B (200 examples) | 10 % | 30 % to 35 % | 60 % or more | 35 % or more |
| B → A (130 examples) | — | — | — | 60 % or more |

METHOD FOR THE ADMINISTRATION OF ANTI-CANCER DRUGS

TECHNICAL FIELD

The present invention relates to an administration method proposing device which proposes an administration method performed in preoperative chemotherapy for operable breast cancer.

BACKGROUND ART

Conventionally proposed on-line software includes software for displaying rates of pCR (Pathological Complete Remission) of early-stage cancers in response to inputs of drug administration procedures for the cancer patients (See NPL1). Here, pCR means a state in which cancer has disappeared almost completely.

However, such software does not propose any drug administration method according to each of types of cancer. For example, breast cancer is roughly classified into four types based on, for example, amounts of protein included in cancer cells. Reactions to the same drug administration vary depending on these cancer types.

FIG. 5 is a diagram showing a conventional drug administration method in preoperative chemotherapy for operable primary breast cancer. The diagram shows a conventionally used regimen (hereinafter referred to as "a JBCRG (Japan Breast Cancer Research Group) 01 trial") indicating firstly performing a cycle (A) for administrating FEC (F:5 fluorouracil in units of 500 mg/m(2), E: epirubicin in units of 100 mg/m(2), and C: cyclophosphamide in units of 500 mg/m(2)) four times every three weeks from six months before an operation, and secondly performing a cycle (B) for administrating docetaxel four times every three weeks in sequence to the cycle (A).

Breast cancer is classified into four types as mentioned above, specifically based on combinations of whether ER (an Estrogen Receptor) is positive or negative and whether Her2 (Human Epidermal growth factor Receptor-2) is positive or negative. Accordingly, pCR values obtained in the JBCRG01 trial are different depending on the types. Hereinafter, "+" denotes positive, and "−" denotes negative. For example, the JBCRG01 trial showed that a high pCR was obtained when the ER/Her2 was (−/+), and a low pCR was obtained when the ER/Her2 was (+/+).

Each of the ER/Her2-(+/+) type and the ER/Her2-(+/−) type has a low pCR in the JBCRG01 trial, but hormonotherapy and radiotherapy other than the operative chemotherapy are available as therapies effective to the types. In contrast, no effective therapy has been found for the ER/Her2-(−/−) type.

Patent Reference 1

Adjuvant! Online; Decision making tools for health care professionals (http://www.adjuvantonline.com/index.jsp)

DISCLOSURE OF INVENTION

Problems that Invention is to Solve

The present invention has been conceived in view of this problem, and has an object to provide an administration method proposing device which proposes an administration method with a high possibility of increasing pCR depending on the cancer types.

Means to Solve the Problems

In order to achieve the above object, an administration method proposing device according to the present invention includes: an input unit configured to receive an input of a cancer type of a cancer patient; a determination unit configured to determine an administration order of a 5-fluorouracil, epirubicin, and cyclophosphamide (FEC) administration cycle and a docetaxel administration cycle, according to an input cancer type; and a display unit configured to display the administration order of the FEC administration cycle and the docetaxel administration cycle, according to a result of the determination by the determination unit. In this way, the administration method proposing device is capable of proposing a more effective anti-cancer drug administration method according to the cancer type of each cancer patient.

Furthermore, an administration method proposing device according to the present invention may cause the determination unit to determine to perform the docetaxel administration cycle before the FEC administration cycle in the case where the input cancer type is indicated by data that an Estrogen Receptor (ER) is negative, and a Human Epidermal growth factor Receptor-2 (Her2) is negative.

It is to be noted that the present invention can be implemented not only as a device, but also as a method having the steps corresponding to processing units of the device, as a program causing a computer to execute these steps, as a recording medium such as a computer-readable CD-ROM on which the program is recorded, and as information, data or a signal representing the program. Furthermore, the program, information, data or signal may be distributed via communication networks such as the Internet.

Effects of the Invention

According to the administration method proposing device of the present invention, it is possible to propose a regimen indicating an administration procedure of drugs that are more effective to a cancer of each of types inputted, in response to each input.

BRIEF DESCRIPTION OF DRAWINGS

FIG. 3 is a diagram showing an example of changes in pCR in the case where the administration order of an FEC administration cycle and a docetaxel administration cycle is reversed.

NUMERICAL REFERENCES

100 Administration method proposing device
101 Input unit
102 Administration procedure determination unit
103 Display unit
104 Display control unit

BEST MODE FOR CARRYING OUT THE INVENTION

An administration method proposing device according to the present invention will be described in detail below with reference to the drawings.

Embodiment

Figure 1:
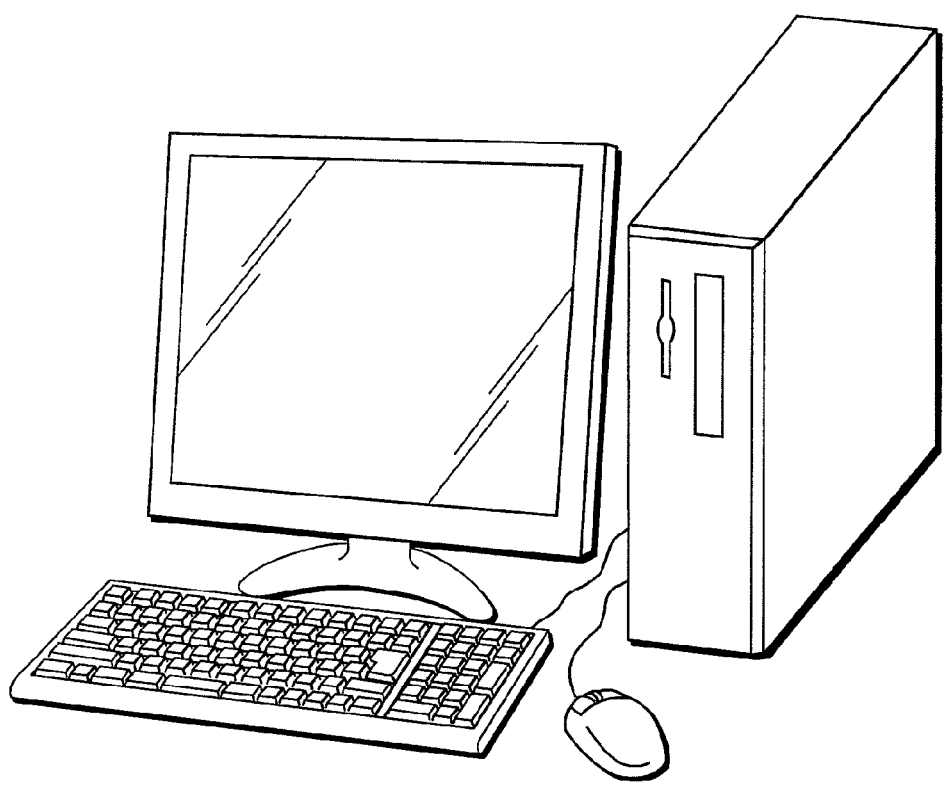
FIG. 1 is a diagram showing an example of an appearance of an administration method proposing device according to the present invention.

FIG. 1 is a diagram showing an example of an appearance of an administration method proposing device according to the present invention. The administration method proposing device according to the present invention proposes a regimen indicating more effective drugs and a procedure for administrating the drugs for a corresponding one of cancer types in response to inputs of the cancer types.

As shown in the diagram, the administration method proposing device according to the present invention is typically implemented as a general computer or a personal computer. The administration method proposing device includes a CPU (Central Processing Unit), a ROM (Read Only Memory), a RAM (Random Access Memory), and an I/O port. Stated differently, this administration method proposing device is implemented by means that a CPU reads out an administration method proposing program recorded on a memory that is ROM, RAM, or the like from the memory, loads the read-out program, and execute the loaded program. The I/O port receives an input of data from outside via a set of keyboards, mouse, USB, or the like.

Figure 2:
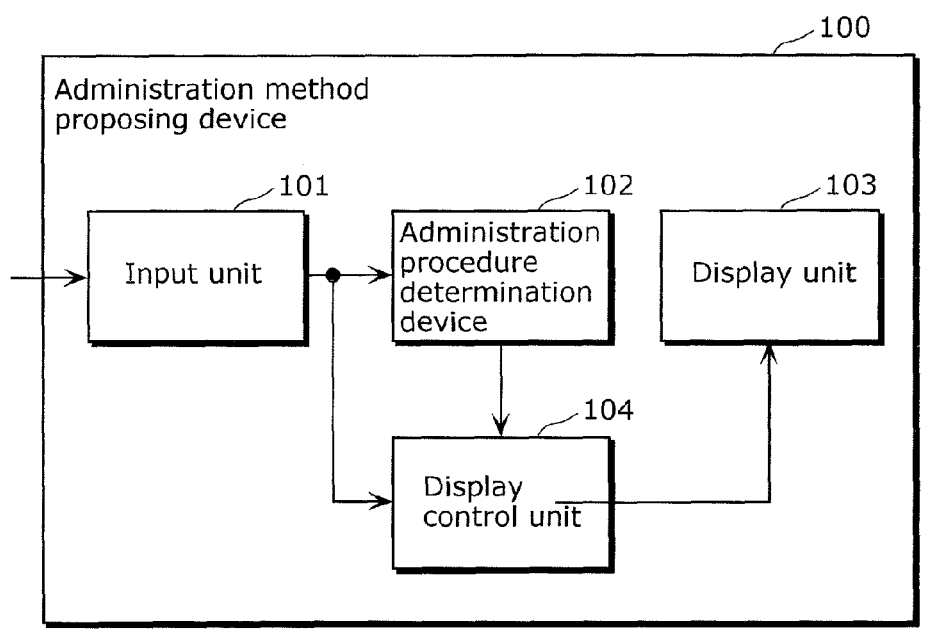
FIG. 2 is a block diagram showing a structure of an administration method proposing device according to the present invention.

FIG. 2 is a block diagram showing a structure of an administration method proposing device 100 according to the present invention. As shown in the diagram, the administration method proposing device 100 includes an input unit 101, an administration procedure determination unit 102, a display unit 103, and a display control unit 104. The input unit 101 is a mouse or set of keyboards that receives inputs from a device operator. For example, the input unit 101 receives inputs of patient-related data such as cancer types together with the names, ages, sexes, disease names of the patients. The administration procedure determination unit 102 determines drug administration procedures depending on the cancer names and types received by the input unit 101. The display unit 103 is a monitor that is a plasma display, a liquid-crystal display, or the like, and displays display image generated by the display control unit 104. The display control unit 104 generates a display image representing a menu screen for guiding the device operator to input and representing the drug administration procedure determined by the administration procedure determination unit 102, and causes the display unit 103 to display the display image.

FIG. 3 is a diagram showing an example of changes in pCR in the case where the administration order of an FEC administration cycle and a docetaxel administration cycle is reversed.

The uppermost row of the table in FIG. 3 shows combinations of ER-positive/negative and Her2-positive/negative which represent breast cancer types. The uppermost row shows ER/Her2-(+/+), ER/Her2-(+/−), ER/Her2-(−/+), and ER/Her2-(−/−) in this sequence from left.

Figure 5:
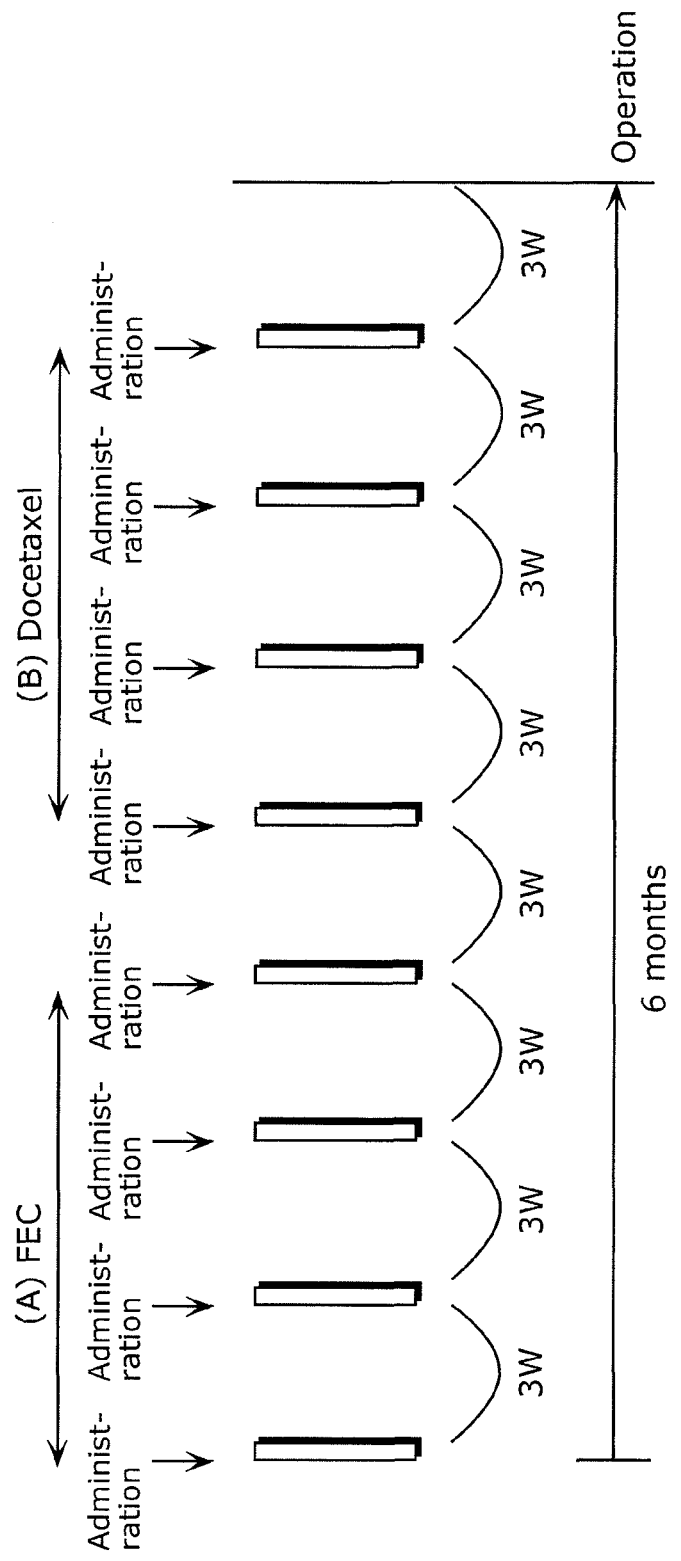
FIG. 5 is a diagram showing a conventional administration example of the FEC administration cycle and the docetaxel administration cycle.

In addition, an example of an administration cycle A→B in the middle row in FIG. 3 shows pCR of each cancer type obtained when 200 patients were subjected to the preoperative chemotherapy as the JBCRG01 trial shown in FIG. 5. The results of the clinical trial show that pCR is 10% in the case of ER/Her2-(+/+), that pCR is 30 to 35% in the case of ER/Her2-(+/−), that pCR is 60% or more in the case of ER/Her2-(−/+), and that pCR is 35% or more in the case of ER/Her2-(−/−).

Further, an example of an administration cycle B→A in the lowermost row in FIG. 3 shows pCR of each cancer type obtained when 130 patients were subjected to the preoperative chemotherapy in which the administration order of the FEC administration cycle and the docetaxel administration cycle was reversed from the administration order in the JBCRG01 trial shown in FIG. 5. Hereinafter, this regimen is referred to as "a JBCRG03 trial". In this case, pCR is 60% or more in the case of ER/Her2-(−/−). This is a remarkable change.

The fact that the pCR is increased to 60% or more in the case of ER/Her2-(−/−) proves a distinguished effect of the administration method in JBCRG03 trial although there had been no effective therapy for the ER/Her2-(−/−) whereas effective therapies other than chemotherapy have been conventionally available for ER/Her2-(+/+), ER/Her2-(+/−), and ER/Her2-(−/+).

Figure 4:
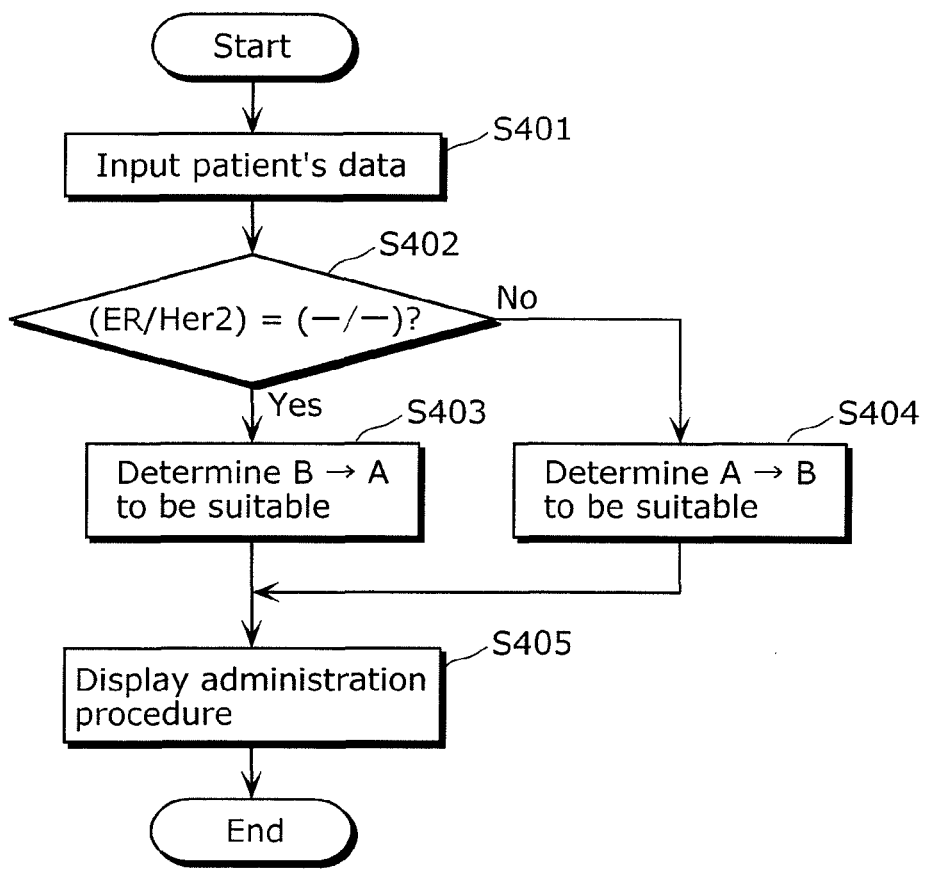
FIG. 4 is a flowchart indicating operations performed by the administration method proposing device according to the present invention.

FIG. 4 is a flowchart indicating operations performed by the administration method proposing device according to the present invention.

First, the input unit 101 receives, from a device operator, an input of patient-related data indicating a cancer type such as ER/Her2 (S401). The administration procedure determination unit 102 determines whether or not the input cancer type ER/Her2 is (−)/(−) (S402). When the input cancer type ER/Her2 is (−)/(−), the administration procedure determination unit 102 determines, to be suitable, a regimen according to the administration cycle B→A indicating the administration order of the docetaxel administration cycle and the FEC administration cycle executed as the JBCRG03 trial (S403). When the input cancer type ER/Her2 is not (−)/(−), the administration procedure determination unit 102 determines, to be suitable, a regimen according to the administration cycle A→B indicating the administration order of the FEC administration cycle and the docetaxel administration cycle executed as the JBCRG01 trial (S404). The display control unit 104 generates a display image for displaying an administration procedure of FEC and docetaxel obtained as a result of the determination by the administration procedure determination unit 102. The administration procedure shows a regimen more effective to an input cancer type. The display unit 103 displays the display image generated by the display control unit 104 (S405).

As described above, the present invention provides an advantageous effect of being able to propose the most effective regimen to each cancer type represented by ER/Her2 or the like in response to the input of each cancer type. The most effective regimen is selectively proposed from among the regimen according to the drug administration procedure in the JBCRG 01 and the regimen according to the reversed drug administration procedure in the JBCRG 03.

All the subjects of the trials are patients who are 60 years old or younger, thus there are no results in the case of patients over 60 years old.

The above Embodiment describes a case where the administration order of the FEC administration cycle and the docetaxel cycle is reversed. However, the present invention is not limited to this, and it is also possible to collect results of clinical study using regimens obtained by reversing the administration orders in the original regimens for various kinds of cancer, and apply the collected results to regimens for other kinds of cancer.

The above Embodiment describes the example in which the FEC administration cycle is four times every three weeks, and the docetaxel administration cycle is four times every three weeks. However, the present invention is not limited to this. For example, the administration method proposing device may propose an FEC administration cycle of three times every three weeks, and a docetaxel administration cycle of three times every three weeks.

The above Embodiment describes the case in which the administration order of the FEC administration cycle and the docetaxel administration cycle is reversed. However, the present invention is not limited to this, and it is also possible to modify the sequential administration cycle orders indicated by regimens, according to cancer types, and propose the modified administration cycle orders.

Furthermore, it is possible to accurately determine the suitability of used regimens by performing pCR tests after the preceding one of the FEC administration cycle and the docetaxel administration cycle.

INDUSTRIAL APPLICABILITY

The present invention is applicable to administration method proposing devices, and in particular to an anti-cancer drug administration method proposing device used in preoperative chemotherapy for breast cancer.

The invention claimed is:

1. A method of treating cancer which is negative for expression of both an Estrogen Receptor (ER) and a Human Epidermal Growth Factor Receptor-2 (HER-2), comprising:
   first determining that the cancer is negative for expression of ER, and negative for expression of HER2;
   second performing a docetaxel administration cycle consisting of administrating docetaxel to a patient multiple times at certain intervals; and then
   third performing a 5-fluorouracil, epirubicin, and cyclophosphamide (FEC) administration cycle comprising administrating 5-fluorouracil, epirubicin, and cyclophosphamide to the patient multiple times at certain intervals.

* * * * *